US011654088B2

(12) United States Patent
Ramana et al.

(10) Patent No.: US 11,654,088 B2
(45) Date of Patent: May 23, 2023

(54) DENTAL ENAMEL COMPOSITIONS WITH ANTI-INFLAMMATORY AGENTS

(71) Applicants: Vivekananda Ramana, Shawnee the Delaware, PA (US); Joel Douglas, Bonita Springs, FL (US)

(72) Inventors: Vivekananda Ramana, Shawnee the Delaware, PA (US); Joel Douglas, Bonita Springs, FL (US)

(*) Notice: Subject to any disclaimer, the term of this patent is extended or adjusted under 35 U.S.C. 154(b) by 0 days.

(21) Appl. No.: 17/580,943

(22) Filed: Jan. 21, 2022

(65) Prior Publication Data

US 2022/0142873 A1 May 12, 2022

Related U.S. Application Data

(63) Continuation of application No. 16/529,202, filed on Aug. 1, 2019, now Pat. No. 11,266,576.

(51) Int. Cl.
| | |
|---|---|
| *A61K 6/836* | (2020.01) |
| *A61K 38/17* | (2006.01) |
| *A61K 31/616* | (2006.01) |
| *A61K 6/54* | (2020.01) |
| *A61K 6/69* | (2020.01) |
| *A61K 6/838* | (2020.01) |

(52) U.S. Cl.
CPC .............. *A61K 6/836* (2020.01); *A61K 6/54* (2020.01); *A61K 6/69* (2020.01); *A61K 6/838* (2020.01); *A61K 31/616* (2013.01); *A61K 38/1767* (2013.01)

(58) Field of Classification Search
CPC ...................................................... A61K 6/836
See application file for complete search history.

(56) References Cited

U.S. PATENT DOCUMENTS

| | | | |
|---|---|---|---|
| 5,268,167 A | 12/1993 | Fung | |
| 5,427,768 A | 6/1995 | Fung | |
| 5,676,720 A | 10/1997 | Ducheyne et al. | |
| 5,981,412 A | 11/1999 | Hench et al. | |
| 6,482,871 B1* | 11/2002 | Aasen | A61K 8/8152 522/90 |
| 6,592,509 B1 | 7/2003 | Hunter, Jr. | |
| 7,361,136 B2 | 4/2008 | Parker | |
| 2004/0086661 A1 | 5/2004 | Yli-Urpo et al. | |
| 2005/0142077 A1 | 6/2005 | Zimmer et al. | |
| 2009/0197221 A1* | 8/2009 | Marshall, Jr. | A61K 6/77 433/217.1 |
| 2018/0110683 A1* | 4/2018 | Yoshinaga | A61K 6/887 |

FOREIGN PATENT DOCUMENTS

WO    WO1997027148 A1    7/1997

* cited by examiner

*Primary Examiner* — Michael F Pepitone
(74) *Attorney, Agent, or Firm* — Joel Douglas; Thomas Ciesco

(57) ABSTRACT

Provided are methods and compositions relating to a dental composition more specifically to prepare the damaged dentin of the tooth prior to repair. The dental compositions include a bioactive glass and a non-aqueous solvent comprising an alcohol, anti-inflammatory and anti-pain reliver.

8 Claims, 6 Drawing Sheets

10  20

DENTAL ENAMEL COMPOSITIONS WITH ANTI-INFLAMMATORY AGENTS

CROSS-REFERENCE TO RELATED APPLICATIONS

This application is a Continuation Utility Patent application claiming priority to U.S. Pat No. 11,266,576, filed on Aug. 1, 2019 which is incorporated by reference herein in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention, and the applicants, make no claim to any trademarks referenced.

BACKGROUND OF THE INVENTION

1) Field of the Invention

The restoration of destroyed or decayed tooth structures can be achieved through the use of various materials including dental amalgams, composite resins, porcelain, or gold. One method used involves the sequential application of a dental adhesive followed by a dental restorative material to the affected tooth structure. Often the affected tooth structure is pretreated to improve the bonding of the adhesive to the dentin or the enamel of the affected tooth structure. For example, the bonding process may include three steps: (1) etching with an inorganic or organic acid to remove surface contaminants and to partially demineralize the dentin matrix; (2) priming with a monomer that can penetrate the collagen-rich network that remains after the etching step; and (3) application of an adhesive resin. The adhesive resin is typically cured to bond to a dental resin composite. Additionally, tooth enamel is the first line of defense against hot, cold, sticky, and abrasive items. When tooth enamel wears down, it can cause tooth decay, exposing dentin and sensitive nerves in the pulp of the teeth, and causing the tooth to appear yellow in color. The enamel can weaken with age. Also, a diet high in sugar content or acidity, and/or a history of acid reflux disease can result in enamel loss.

U.S. Pat. Application 200901977221, herein incorporated by reference describes dental bonding slurry and U.S. Pat. Application 20050142077, herein incorporated by reference describes the use of antimicrobial glass ceramic in dental care.

However, glasses having a bioactive and, also, sometimes antimicrobial effect are described as bioglass in An Introduction to Bioceramics, World Scientific Publ. (Hensch and Wilson, 1993). Bioglass of this type is distinguished by the formation of hydroxylapatite layers in aqueous media. Heavy metal free alkali and alkaline earth silicate glasses having antimicrobial properties are described in the applications DE-A-199 32 238 and DE-A-199 32 239, herein incorporated by reference in its entirety.

A glass powder that includes 40-60 weight-percent $SiO_2$, 5-30 weight-percent $Na_2O$, 10-35 weight-percent CaO, and 0-12 weight-percent P2Os is known from U.S. Pat. No. 5,676,720 herein incorporated by reference in its entirety, a glass ceramic manufactured from a glass of this type of composition also being known. However, no information about the crystal phase is given in U.S. Pat. No. 5,676,720.

U.S. Pat. No. 5,981,412, herein incorporated by reference in its entirety describes a bioactive bioceramic for medical applications having the crystalline phase Na2O.2CaO3SiO2. The crystallite size is 13 μm. The ceramization is performed using tempering steps for nucleation and crystallization. The emphasis is on mechanical properties such as K1c. The crystal phase component is between 34 and 60 volume-percent. U.S. Pat. No. 5,981,412, herein incorporated by reference in its entirety only describes a crystalline phase that is a high-temperature phase and that only arises under the special conditions specified in this publication. An application in the field of dental care is not described.

The use of bioactive glasses for toothpaste and gels is described, for example, in WO 97/27148, herein incorporated by reference in its entirety. Inorganic non-metallic materials that contain calcium and phosphorus and lead to tooth remineralization through appropriate ion donations are known from U.S. Pat. Nos. 5,427,768 and 5,208,167, herein incorporated by reference in its entirety.

All the above publications and patents cited in this specification are herein incorporated by reference as if each individual publication or patent were specifically and individually indicated to be incorporated by reference and are incorporated herein by reference to disclose and describe the methods and/or materials in connection with which the publications are cited.

However, the prior art does not solve the issues associated with the dentin and enamel reconstruction and due to inflammation, infection and the slow assimilation of the bioglass into the dentin structure. The instant invention provides solutions to these issues.

None of the aforementioned references describes the use of bioactive glass applied to the existing exposed dentin due to loss of enamel that causes the tooth to appear yellow. The use of bioactive glass will be shown to retard the effect of staining and provide a mechanism to enhance light reflection, so the tooth appears whiter than the native dentin exposed due to enamel loss.

However, glasses having a bioactive and, also, sometimes antimicrobial effect are described as bioglass in An Introduction to Bioceramics, World Scientific Publ. (Hensch and Wilson, 1993). Bioglass of this type is distinguished by the formation of hydroxylapatite layers in aqueous media. Heavy metal free alkali and alkaline earth silicate glasses having antimicrobial properties are described in the applications DE-A-199 32 238 and DE-A-199 32 239, herein incorporated by reference in its entirety.

A glass powder that, includes 40-60 of the total weight percent is SiO2, 5-30 of the total weight percent is $Na_2O$, 10-35 of the total weight percent is CaO, and 0-12 of the total weight percent is $P_2O_5$ is known from U.S. Pat. No. 5,676,720 herein incorporated by reference in its entirety, a glass ceramic manufactured from a glass of this type of composition also being known. However, no information about the crystal phase is given in U.S. Pat. No. 5,676,720.

U.S. Pat. No. 5,981,412 are herein incorporated by reference in its entirety describes a bioactive bioceramic for medical applications having the crystalline phase $Na_2O2CaO.3SiO_2$. The crystallite size is 13 μm. The ceramization is performed using tempering steps for nucleation and crystallization. The emphasis is on mechanical properties such as $K_1c$. The crystal phase component is between 34 and 60 volume-percent. U.S. Pat. No. 5,981,412, herein incorporated by reference in its entirety only describes a crystalline phase that is a high-temperature phase and that only arises under the special conditions specified in this publication. An application in the field of dental care is not described. U.S. Pat. Application 200901977221, herein incorporated by reference in its entirety describes dental bonding slurries and U.S. Pat. Application 20050142077, herein incorporated by reference in its entirety describes the use of antimicrobial glass ceramic in dental care.

The use of bioactive glasses for toothpaste and gels is described, for example, in WO 97/27148, herein incorporated by reference in its entirety. Inorganic non-metallic materials that contain calcium and phosphorus and lead to tooth remineralization through appropriate ion donations are known from U.S. Pat. Nos. 5,427,768 and 5,268,167, herein incorporated by reference in its entirety. U.S. Patent application 2009/019722 describes a method and compositions relating to a dental bonding slurry useful in bonding a dental resin composite herein incorporated by reference in its entirety.

The use of the glasses cited above in the fields of dental care and/or oral hygiene do not identify the ability for the glass to be used to increase the perception of whiteness of the tooth. Additionally, all the above publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The instant invention solves the problems of using peroxides by creating a dental bonding slurry formed from bioactive glass and a suitable non-aqueous solvent, for the first time, an effective dental bonding method is provided that does not utilize excessive bleaching or contains a large concentration of hydrogen peroxide.

The instant invention also provides a means of mitigating the pain and discomfort associated with the process of repairing and dental bonding the dentin as well as a method to reduce the discomfort and pain to the individual, reduce inflammation, infection and assist in bone resorption from bone loss.

BRIEF SUMMARY OF THE INVENTION

The disclosure provides methods and compositions relating to a dental bonding slurry useful in bonding a dental resin composite. Teeth are protected by enamel, their first defense against hot, cold, sticky, and abrasive items. When enamel wears down, it can cause tooth decay, exposing dentin and sensitive nerves within the pulp of the teeth, and causes the tooth to look yellow. Enamel can become weaker with age, an acidic or sugary diet, and/or a history of acid reflux disease. Additionally, dentin hypersensitivity is observed after periodontal treatment in periodontitis patients. The invention focuses on the dentinal tubule, one of the very small tubes or canals in the dentin. These tubules are responsible for dentin hypersensitivity. The dentin tubules extend from the pulp cavity of the tooth to the enamel and are occupied by odontoblastic processes and occasional nerve filaments. In addition to occluding the dentin tubule with a micro-mechanical bond the invention discloses a means to increase the strength of the hydroxyapatite on surface of the tooth enamel and increase the fluidity flow of the slurry/gel into the dentin to create a much stronger bond and prevent microleakage/sensitivity. It is long known that the bioglass can, in the aqueous presence of calcium and phosphate, form apatite to further prevent sensitivity and lock out micro-leakage through the tubules. However, the time for the calcium and phosphate apatite to form a bond is an issue with the patient acceptance of the treatment.

In addition to occluding the dentin tubule with a micromechanical bond, it is long known that the bioglass can, in the aqueous presence of calcium and phosphate, form apatite to further prevent sensitivity and lock out micro-leakage through the tubules and increase the appearance of whiter enamel structure. However, the process can result in pain for the patient and a method is needed to minimize the pain. To mitigate the pain the instant invention primary therapeutic ingredients, use a combination of natural products designed to reduce the problems with inflammation and pain as well as aspirin, or acetylsalicylic acid (ASA) which is a known anti-inflammatory and pain reliever. The natural products include Neem or Nimba, *Punica granatum*, Menta spp. clove oil, Cannabidiol (CBD) oil, Boswellia and chlorotoxin and other inflammation and pain agents. By adding these treatment agents to the suspension of the instant invention the result is minimization of pain and discomfort associated with the exposed dentin and with the process of repair and dental bonding the dentin.

Neem or Nimba leaf extract is used for gum disease (gingivitis), kill bacteria and prevent plaque formation in the mouth.

*Punica granatum* (Pomegranate) is one of the oldest edible fruit which has a long history as a medicinal fruit. *Punica granatum* has a preventive and therapeutic aid to inflammation periodontal disease.

*Menta* spp. is considered an anti-infective and aroma.

While many of the components of the mixture therapeutic benefits are well known the following are benefits are highlighted. Neem (*Azadirachta indica*), is a member of the Meliaceae family, has therapeutics implication in the diseases prevention and treatment. It is considered that *Azadirachta indica* shows therapeutic role due to the rich source of antioxidant and other valuable active compounds such as azadirachtin, nimbolinin, nimbin, nimbidin, nimbidol, salannin, and quercetin.

*Punica granatum* is known for having high antioxidant activity and Menta spp. is considered an anti-infective and aroma as well as antispasmodic and anti-inflammatory effects.

A potential source of effective chlorotoxin's is the venom from Scorpions that are part of the order Scorpiones and the class Arachnida. They are invertebrates that possess eight legs and a two-segmented body composed of a cephalothorax and abdomen. This is the classification of scorpions: Kingdom Animalia (Animals); Phylum: Arthropoda (Arthropods); Subphylum: Chelicerata; Class: Arachnida (Arachnids); and Order: Scorpiones (Scorpions). Current records show that there are 1,004 known species. The number of species and the potential of compounds from the more than 1000 known species combined with the knowledge base of both native American, Indian homeopathic medicine and other homeopathic literature indicate that there is a wealth of opportunity in the chlorotoxin's of scorpion species to elevate the symptoms of effective treatments to disease states such as heart disease, cancer, Alzheimer's, epilepsy, inflammation and pain management.

Research to date shows that natural based formulations especially comprised of natural materials such as CDB and clove oil and natural chlorotoxins can be used for targeting cancer, heart disease, Alzheimer's, epilepsy, inflammation and pain management.

Hence, there is need for a formulation for treating exposed dentin which is the result of loss of protective enamel comprised of promising natural based formulations, especially CBD and clove oil and natural chlorotoxins, for targeting inflammation and pain and with less or no side effects. Also, there is a need for a method for synthesizing the formulation comprising clove oil and CBD and natural chlorotoxins for minimizing inflammation and pain in dental work.

There is also a need to improve the reduce the bond time and increase the bond between the bioglass and the treated dentin.

Accordingly, the present disclosure provides methods repairing teeth that have been affected by the loss of enamel. In certain embodiments, such methods include, first, applying a diluted hydrogen peroxide mixture to the teeth, and then, applying an etching composition comprising an etchant to a tooth to etched the exposed dentin surface that has been exposed by the loss of enamel; applying a non-aqueous solvent composition to the etched dentin surface; the non-aqueous solvent composition includes a bioactive glass substantially lacking silanol groups, and a non-aqueous solvent to the primed exposed dentin surface, and where the non-aqueous solvent composition provide for formation of a hybrid layer, where the hybrid layer comprises dentin and the bioglass composition. However, the process and the effect of loss of enamel has many negative repercussions for the patient. The instant invention over comes the issues of inflammation, infection, pain and bone resorption from bone loss which are associated with the loss of dentin.

To reduce the time, reduce the bond time and increase the bond between the bioglass and the treated dentin the instant invention provides methods that utilizes electromagnetic field.

The acid etch step in the tooth restoration process exposes the dentin tubules. The diameter of the open tubules measures about 1 μm. To allow penetration into the tubules, the bioglass has been manufactured to a particle size of less than 1 μm maximum. By adding a combination of clove oil, Cannabidiol (CBD) oil, Boswellia and chlorotoxin and other inflammation and pain agents the instant invention minimizes pain and discomfort associated with the exposed dentin and with the process of repair and dental bonding the dentin. The particle size of less than 1 μm of the bioglass particles are found to penetrate deeper into the tubules creating a reflective surface that will appear white when exposed to normal lighting conditions. The penetration of the glass particles also carries the anti-inflammatory and pain relieve agents into the tubules and reduce the inflammation and pain associated with the condition and the procedure. In addition to occluding the dentin tubule with a micro-mechanical bond, it is long known that the bioglass can, in the aqueous presence of calcium and phosphate, form apatite and when the bioglass is subjected to the proper electromagnetic field the bond time is reduced and the bond between the bioglass and the treated dentin is increase. Specifically, the electromagnetic stimulator increase the bond strength, bioactivity and promotes the formation of carbonated hydroxyapatite MCA).

In exemplary embodiments, the bioactive glass has the following approximate composition by weight percentage: 49.5% of the total weight of bioactive glass comprising of $SiO_2$, 17% of the total weight of bioactive glass comprising of $Na_2O$, 26.9% of the total weight of bioactive glass comprising of CaO, 6.6% of the total weight of bioactive glass comprising of $P_2O_5$. In further embodiments, the bioactive glass has an average particle size of 1 μm or less. In still further embodiments, the dental bonding slurry has about 0.5% to about 40% by weight of said bioactive glass. In an exemplary embodiment, the alcohol solvent is ethanol. The anti-inflammatory and pain reliever components contribute between 0.01 to 5% of the total weight of the preparation.

Also provided are kits containing the dental bonding slurry for use in the subject methods. In certain embodiments, the kits may include a dental bonding slurry or gel format that comprises a bioactive glass substantially lacking silanol groups and a non-aqueous solvent comprising an alcohol, anti-inflammatory and pain reliever and, optionally, an etching composition. In further embodiments, the kit may include the dental bonding slurry provided as separate components, where a first component comprises the bioactive glass in the non-aqueous solvent, where the first component is provided in a container. In further embodiments, the kit may include the dental bonding slurry provided as separate components, where a first component comprises the bioactive glass and the second container the non-aqueous solvent having anti-inflammatory and pain reliever dissolved in the non-aqueous solvent.

These and other objects, features, and advantages of the present invention will become more readily apparent from the attached drawings and the detailed description of the preferred embodiments, which follow.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

Corresponding reference characters indicate corresponding parts throughout the several views. The exemplifications set out herein illustrate embodiments of the invention and such exemplifications are not to be construed as limiting the scope of the invention in any manner.

Definitions

Figure 1:
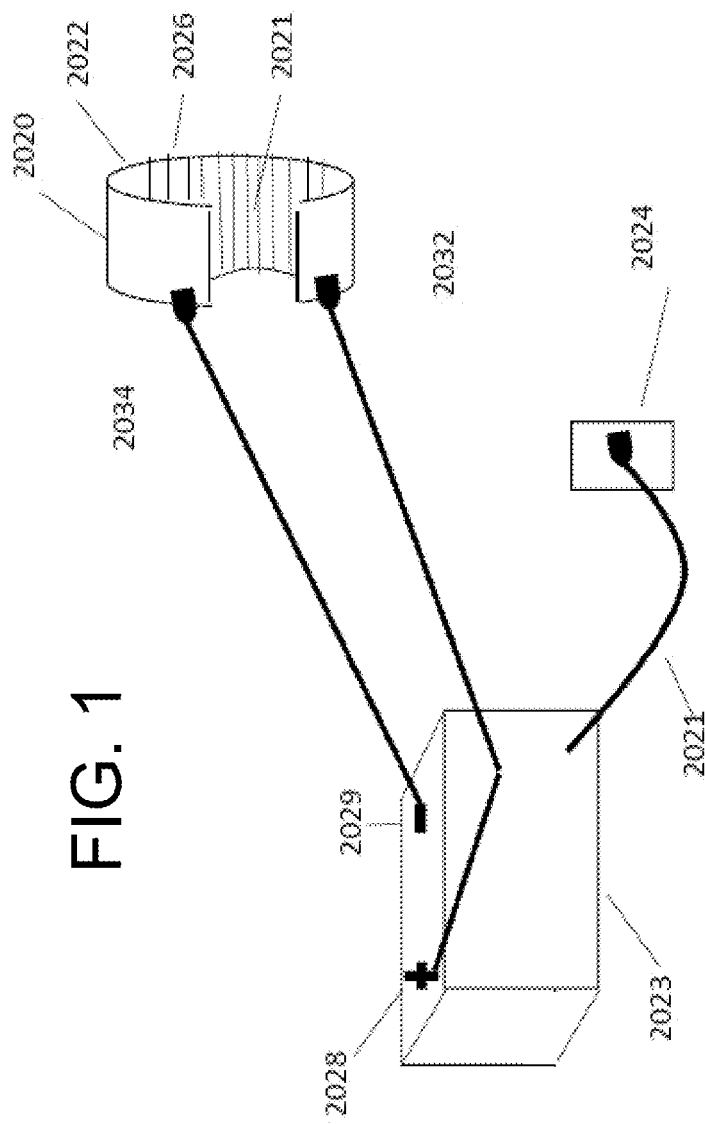
FIG. 1 shows an electromagnetic field stimulator to reduce the bond time and increase the bond between the bioglass and the treated dentin.

The term "dentin" as used herein refers to a calcified tissue of the body that is one of the major components of teeth. Dentin is usually covered by enamel that forms the outer surface of the tooth. Dentin is a porous matrix composed of up to 70% hydroxyapatite. Dentin has microscopic channels called dentinal tubules that span the thickness of the dentin. Dentinal tubules taper in diameter from the inner to the outermost surface of the dentin, having a diameter of about 2.5 μm near the inner surface of the dentin, about 1.2 μm in the middle of the dentin, and about 900 nm near the outer surface of the dentin. In addition, dentinal tubules are surrounded by collagen fibers that form an extensive collagen network.

The term "prime" or "priming" as used herein means applying a compound to an acid-etched surface of a tooth to facilitate stabilization of the collagen network in the demineralized dentin, such as may result from an etching process. Dental primers also include self-etching primers, which achieve the steps of etching and priming in a single application step. Self-etching primers may include acidic monomers. Thus, reference to an "etched and primed surface" is meant to encompass etching and priming in separate steps or in a single step.

The terms "dental resin adhesive", "dental adhesive", "adhesive", "adhesive resin", or "resin-based adhesive" as used herein refer to compounds useful in facilitating a bond between a dental resin composite to a tooth. Adhesives may include a mixture of monomeric molecules that polymerize upon curing. Adhesives may be cured using light or a catalyst. Dental adhesives also include self-etching adhesives. A self-etching adhesive is an adhesive that contains compounds (i.e., a self-etching primer, such as an acidic monomer, and an adhesive) that achieve the steps of etching, priming, and bonding in a single application step.

The term adhesives can be "unfilled", wherein the adhesive is composed of compounds that actively participate in the polymerization and bonding process. Adhesives can be "filled", wherein the adhesive contains compounds that do not participate in the polymerization and bonding process. Examples of fillers include, but are not limited to, silica powder, glass beads, aluminum oxide powder, iron oxide and quartz powder.

The term "etch" or "etching" as used herein means either applying an acid to the surface of a tooth to partially dissolve the apatite or utilizing a bristle brush to produce irregularities in the surface of dentin.

The terms bioglass and bioactive glasses are used interchangeably and may contain but are not limited to silicon, dioxide), sodium oxide, calcium oxide, magnesium oxide, phosphorous pentoxide, and calcium fluoride. Other components may be added such as boron, magnesium, aluminum, iron, titanium, fluorine, and silver. The addition of fluorine to bioactive glass can be rationalized for the following reasons: firstly, that the rate of apatite formation at the glass surface can be enhanced; and secondly, that the apatite formed will be less vulnerable to acid attack, both of which are desirable in bioactive glass to be utilized in dental applications. Magnesium may also be added to bioactive glass, as it has been shown to slow down the rate of apatite precipitation, thus leading to more controlled mineralization.

The term "hybrid layer" where the hybrid layer comprises dentin and the bioglass composition.

The term "chlorotoxins" as used herein means a wino acid basic peptide from the venom of the scorpion.

The term slurry and Gel are used interchangeably.

The term scorpion refer to arthropods that are members of Arachnida class and order Scorpiones based compounds. For this example, the Blue Scorpion Venom Chlorotoxin venom is extracted by a mild electro-stimulation method, that, includes stimulating and scorpion restraining devices. However, researchers have had success milking scorpions in the Buthidae family, the Scorpionidae family which includes the emperor scorpion (*Pandinus imperator*), and the *Heterometrus swammerdami* scorpion as well as specific species such as African *Androctonus australis*, *Hadrurus hirsutus*, Albino Scorpions, Black Scorpions or Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions and Whip Scorpions.

The terms "substantially asks" or "substantially lacking" as used herein refer to a compound that is at least about 60% free, or about 75% free, or about 90-95% free from a component. For example, "substantially lacking, silanol groups" refers to a compound that is at least about 60% free, or about 75% free, or about 90-95% free of silanol groups.

The term "non-aqueous solvent" is meant to encompass solvents that do not contain water as a predominant component, and includes solvents that contain, for example, less than 15% water by volume, less than 10% water by volume, less than 5% water by volume, less than 1% water by volume, and may contain no detectable water.

The terms anti-inflammatory and pain reliever include compositions clove oil, Cannabidiol (CBD) oil, Boswellia and chlorotoxin and other inflammation and pain agents such as Aspirin, or acetylsalicylic acid (ASA).

The term NSAIDs means Nonsteroidal anti-inflammatory drugs (NSAIDs) which block the enzyme cyclooxygenase known as COX enzymes and reduce prostaglandins throughout the body. As a consequence, ongoing inflammation, pain, and fever are reduced. They include aspirin, celecoxib, diclofenac, diflunisal, etodolac, ibuprofen, indomethacin, ketoprofen, ketorolac, nabumetone, naproxen, oxaprozin and piroxicam.

DETAILED DESCRIPTION OF THE INVENTION

Exemplary embodiments of the methods and compositions of the present disclosure are provided below. These include methods of utilizing natural products to reduce the inflammation and pain of gums and gumline, nerves and methods for preparing dentin for bonding to a dental resin composite, methods for forming an adhesive bond between a dental resin composite and dentin, methods for making an adhesive composition useful in such methods, and methods to reduce the bond time and increase the bond between the bioglass and dentin, and kits useful in such methods.

Before the present invention is described in greater detail, it is to be understood that this invention is not limited to embodiments described, as such may, of course, vary. It is also to be understood that the terminology used herein is for the purpose of describing embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention, Further, the dates of publication provided may be different from the actual publication dates that may need to be independently confirmed.

It must be noted that as used herein and in the appended claims, the singular forms "a", "an", and "the" include plural referents unless the context dearly dictates otherwise. It is further noted that the claims may be drafted to exclude any element, including optional elements. As such, this statement is intended to serve as antecedent basis for use of such exclusive terminology as "solely", "only", and the like in connection with the recitation of claim elements, or use of a "negative" limitation.

U.S. Patent application 200919722 discloses a method of using bioglass to treat detin prior to enamel restoration. The disclosure U.S. Patent application 2009197221 is hereby incorporated by reference in its entirety. However, the process disclosed does not provide an anti-inflammatory agent or chlorotoxin component to the mixture that is capable of reducing pain, inflammation and infection.

As will be apparent to those of skill in the art upon reading this disclosure, each of the individual embodiments described and illustrated herein has discrete components and features that may be readily separated from or combined with the features of any of the other several embodiments without departing from the scope or spirit of the present invention. Any recited method can be carried out in the order of events recited or in any other order that is logically possible.

The compositions for desensitizing agent for dentin surface of the present disclosure will be described first, followed by a detailed description of exemplary uses for the compositions for desensitizing agent for dentin surface.

Compositions for Desensitizing Agent for Dentin Surfaces

A composition for preparing dentin for bonding to a dental resin composite is provided. The term "dental bonding slurry" is intended to refer to any mixture of anti-inflammatory and pain relievers incorporated into a bioactive glass-containing composition that can find a use in one or more steps as a dentin tubule agent according to the present disclosure. As noted earlier, enamel erosion occurs when enamel wears down, it can cause tooth decay, exposing dentin and sensitive nerves within the pulp of the teeth, and causes the dentin to be exposed which results in significant inflammation and pain associated with the condition.

Thus, dental bonding slurry compositions include, but are not necessarily limited to, compositions comprising a suitable anti-inflammatory and pain reliever incorporated into a non-aqueous solvent (e.g., an alcohol such as ethanol) and bioactive glass (e.g., to be applied to an etched dentin surface) mixture used to repair the dentin. The bioactive glass present in the dental bonding slurry is generally a bioactive glass that substantially lacks silanol groups. The anti-inflammatory and pain relievers incorporated into the dental bonding slurry include mixtures and combinations of clove oil, Cannabidiol (CBD) oil, Boswellia and chlorotoxin and other inflammation and pain agents such as Aspirin, or acetylsalicylic acid (ASA). The instant invention minimizes pain and discomfort associated with the exposed dentin and with the process of repair and dental bonding the dentin. Exemplary dental bonding slurry's are described in more detail below.

The medical literature in India and the traditional system of medicines and classical records provide details of the pain management techniques that utilize small amounts of scorpion venom and the natural products including Cannabidiol (CBD) oil, Boswellia. In nature, scorpion chlorotoxins immobilize the envenomated prey. Research has shown that chlorotoxins bind preferentially and are capable of relieving pain. The present disclosure provides various embodiments of the present invention. The embodiments provide a formulation/composition comprising phytonutrients and natural chlorotoxins for targeting pain and inflammation without any side effects. The embodiments of the present invention also provide a method for the synthesis of a formulation comprising phytonutrients including Cannabis sativa (cannabinoids) and natural chlorotoxins for targeting inflammation, pain, and infections. (as discussed in Mediators of Inflammation Volume 2010 (2010), Article ID 903295, http://dx.doi.org/10.1155/2010/903295, Scorpion Venom and the Inflammatory Response by Vera L. Petricevich)

In certain cases, the dental bonding slurry can include natural products such as clove oil, Cannabidiol (CBD) oil, Boswellia and chlorotoxin and other inflammation and pain agents such as Aspirin, or acetylsalicylic acid (ASA) or other NSAID pain relive medication. The Cannabidiol (CBD), Boswellia and chlorotoxin which are known anti-inflammatory and pain reliever agents when suspended in a mixture containing a bioactive glass substantially lacking silanol groups and a non-aqueous solvent comprising an alcohol creates a minimal pain material composition useful in treating dentin restoration and dental bonding. When incorporated into a bioactive glass and a suitable non-aqueous solvent then the mixture is useful in treating dentin restoration and dental bonding. In some cases, the dental bonding slurry can comprise from about 0.5% to about 40% by weight of the bioactive glass. In cases where a higher weight % of the bioactive glass is described, suspension of the bioactive glass in a suitable non-aqueous solvent may be facilitated by use of a bioactive glass powder having a smaller average particle size (e.g., less than 1 µm average particle size, preferably 0.5 µm) or less. The anti-inflammatory and pain reliever components contribute between 0.01 to 5% of the total weight of the preparation. The kit can also include an electromagnetic stimulator which provides electromagnetic exposure as treatment procedure to increase the bond strength of the bioactive glass by promoting bioactivity and the formation of carbonated hydroxyapatite (HCA).

In one embodiment, the dental bonding slurry can include natural products such as clove oil, Cannabidiol (CBD) oil, Boswellia and chlorotoxin and other inflammation and pain agents such as aspirin, or acetylsalicylic acid (ASA) or other NSAID pain relive medication. The Cannabidiol (CBD), Boswellia and chlorotoxin which are known anti-inflammatory and pain reliever agents when suspended in a mixture containing and a bioactive glass suspended in a suitable non-aqueous solvent (e.g., a slurry). In these embodiments, the dental bonding slurry comprises about 5% by weight, about 10% by weight, about 15% by weight, about 20% by weight, about 25% by weight, about 30% by weight, about 35% by weight, or about 40% by weight, or more, of the bioactive glass. The anti-inflammatory and pain reliever components contribute between 0.01 to 5% of the total weight of the preparation. The anti-inflammatory agents can be selected from clove oil, Cannabidiol (CBD) oil, Boswellia and chlorotoxin and other inflammation and pain agents such as aspirin, or acetylsalicylic acid (ASA) or other NSAID pain relive medication. The amount of bioactive glass incorporated into the dental bonding slurry can vary with the average particle size of the bioactive glass. Smaller average particle sizes (e.g., 1 μm or less) may allow for more bioactive glass to be suspended in the dental bonding slurry mixture.

In certain, cases, the dental bonding slurry can include natural products such as clove oil, Cannabidiol (CBD) oil, Boswellia and chlorotoxin and other inflammation and pain agents such as aspirin, or acetylsalicylic acid (ASA) or other NSAID pain relive medication. The Cannabidiol (CBD), Boswellia and chlorotoxin which are known anti-inflammatory and pain reliever agents when suspended in a mixture containing and a bioactive glass used in the dental bonding slurry is Bioglass 45S5 and has the following approximate composition by weight percentage: 49.5% of the total weight percent is $SiO_2$, 17% of the total weight percent is $Na_2O$, 26.9% of the total weight percent is CaO, 6.6% of the total weight percent is $P_2O_5$. In other cases, the bioactive glass used in the dental bonding slurry is Bioglass F glass and has the following approximate composition by weight percentage: 44% of the total weight percent is $SiO_2$, 23% of the total weight percent is $Na_2O$, 10% of the total weight percent is CaO, 4.5% of the total weight percent is MgO, 6% of the total weight percent is $P_2O_5$, 12.5% of the total weight percent is $CaF_2$. The anti-inflammatory and pain reliever components contribute between 0.01 to 5% of the total weight of the preparation. In either case, the bioactive glass used in the dental bonding slurry may have an average particle size of 1 μm or less and preferably 0.5 μm. Bioglass 45S5 or Bioglass F powders may be prepared by methods known to those of skill in the art, including but not limited of sintering process to achieve maximum compressive strength and high energy ball milling of bioglass.

The bioactive glass is dispersed in the dental bonding slurry via a solvent. The solvent is preloaded with the anti-inflammatory mixture such that the dental bonding slurry can include natural products such as clove oil, Cannabidiol (CBD) oil, Boswellia and chlorotoxin and other inflammation and pain agents such as aspirin, or acetylsalicylic acid (ASA) or other NSAID pain relive medication. The anti-inflammatory and pain reliever components contribute between 0.01 to 5% of the total weight of the preparation. The Cannabidiol (CBD), Boswellia and chlorotoxin which are known anti-inflammatory and pain reliever agents when suspended in a mixture containing and a bioactive glass. As discussed below, the water content of the solvent is selected so that reaction of the bioactive glass with water in the solvent is insignificant, and may be so low as to avoid such reaction.

The key to the dental bonding slurry performance anti-inflammatory and palm oil that allow penetration into the tubule. By adding a combination of clove oil, Cannabidiol (CBD) oil, Boswellia and chlorotoxin and other inflammation and pain agents the instant invention minimizes pain and discomfort associated with the exposed dentin and with the process of repair and dental bonding the dentin. The bioglass is then added to the mixture and the small particle size distribution, 1 μm maximum of the bioglass component are designed to allow them to fill the dentinal tubules. The acid etch step in the tooth restoration process exposes the dentinal tubules. The diameter of the open tubules measures about 1 μm, therefore, the bioglass must have a maximum dimension of less than 1 μm, preferably 0.5 μm. To allow penetration into the dentinal tubules, bioglass needs to be manufactured to a particle size of less than 1 μm and preferably 0.5 μm. At this size, the particles are found to penetrate deeper into the tubules and will result in improved sealing. In addition to occluding the dentinal tubule with a micro-mechanical bond, it is long known that the bioglass can, in the aqueous presence of calcium and phosphate, form apatite to further prevent sensitivity, lock out micro-leakage through the tubules, and increase the appearance of a whiter color enamel structure. However, the time to achieve bond strength and the bond the bonding time needs to be reduced.

The dental bonding slurry theoretically has the added benefit of facilitating the inhibition of leakage of particulate materials and/or fluid from the dentin or oral environment treated with the dental bonding slurry. Inhibition of leakage can include both microleakage and nanoleakage. Microleakage is the seepage of fluids, debris, and/or microorganisms (e.g., bacteria) into micrometer-sized gaps (approximately $10.\sup-6$ m) between any dental restoration and a tooth. Nanoleakage is the seepage of fluids, debris, and/or microorganisms (e.g. bacteria) into nanometer-sized gaps (i.e., approximately $10.\sup-9$ m) between any dental restoration and a tooth. Without being held to theory, the ability of bioactive glasses to promote the formation of apatite in aqueous environments that contain calcium and phosphate (e.g., saliva) can facilitate inhibition of leakage at the bonded interface through a mechanism of self-sealing due to the formation of apatite. This sealing prevents the intrusion of materials that would further discolor the tooth. The instant invention has shown that applying electromagnetism immediately after the application of the dental bonding slurry improves the bond strength and reduces the bonding time required. This means that the enamel restoration process can be performed on the patient sooner than previous treatment methods.

The example utilizes the Blue Scorpion Venom Chlorotoxin venom however the opportunity to expand the viable chlorotoxin pool of compounds by utilizing any one of the more than 1004 known species of scorpion's in the treatment of disease's such as heart disease, cancer, Alzheimer's, epilepsy, inflammation and pain management is incorporate because any one of the vast number of scorpion's could be used as a donor animal and this specification includes the incorporation of any of these animals being used as an alternative sources of chlorotoxin's. For this example, the Blue Scorpion Venom Chlorotoxin venom is extracted by a mild electro-stimulation method, that includes stimulating and scorpion restraining devices. However, researchers have had success milking scorpions in the Buthidae family, the Scorpionidae family which includes the emperor scorpion (*Pandinus imperator*), and the *Heterometrus swammerdami* scorpion as well as specific species such as African *Androctonus australis, Hadrurus hirsutus*, Albino Scorpions, Black Scorpions or Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions and Whip Scorpions.

Once the venom is extracted, it is frozen and then lyophilized into a powder form that can be added to the ethanol slurry in the ratio 1-part venom 10,000 parts by weight of ethanol, then mixing thoroughly. The 1-part venom to 10,000 parts ethanol is preferred. However, clinically effective slurries with ratios from 1 to 1000 parts venom and 1000 to 20000 parts by weight ethanol have been made successfully.

Bioactive Glass Compounds

Bioactive glasses elicit a series of chemical reactions when they are brought into contact with an aqueous environment that contains calcium and phosphate, such as bone or tissue, leading to the formation of carbonated hydroxyapatite (HCA), similar to the mineral that forms teeth. The formation of HCA creates a bond between the bioactive glass and the dentin. The bond may be a mechanical bond and/or due to a chemical interaction between the bioactive glass and the dentin, forming HCA bonds to specific amino acids within the collagen matrix of the dentin.

Bioactive glasses may contain, but are not limited to, silicon dioxide ($SiO_2$), sodium oxide ($Na_2O$), calcium oxide (CaO), magnesium oxide (MgO), phosphorous pentoxide ($P_2O_5$), and calcium fluoride ($CaF_2$). Other components may be added, such as boron, magnesium, aluminum, iron, titanium, fluorine, and silver. The addition of fluorine to bioactive glass can be rationalized for the following reasons: firstly, that the rate of apatite formation at the glass surface can be enhanced; and secondly, that the apatite formed will be less vulnerable to acid attack; both are desirable in bioactive glass to be utilized in dental applications. Magnesium may also be added to bioactive glass, as it has been shown to slow down the rate of apatite precipitation, thus leading to more controlled mineralization.

Bioactive glass for use in the compositions and methods disclosed herein generally are characterized by having predominantly more silicon dioxide ($SiO_2$) groups than silanol ($H_3SiOH$) groups. This improves the dental bonding. In general, this can be achieved by avoiding bioactive glass contact with water and/or hydrogen atoms, thereby inhibiting production of silanol in the bioactive glass composition (e.g., as by the reaction $Si—O—Na^+H_++OH^-\rightarrow Si—OH^+ + Na^+ + OH.^-$). Accordingly, bioactive glass can be described as having as a total of $SiO2$ and $H3\,SiOH$ groups, greater than 50% $SiO_2$ groups, greater than 60% $SiO_2$ groups, greater than 75% $SiO_2$ groups, greater than 85% $SiO_2$ groups, greater than 90% $SiO_2$ groups, greater than 95% $SiO_2$ groups, and can be described as having, as a total of $SiO_2$ and $H3SiOH$ groups, at least 55% $SiO2$ groups, at least 65% $SiO_2$ groups, at least 80% $SiO_2$ groups, at least 90% $SiO_2$ groups or more. In some embodiments, the bioactive glass is characterized as "substantially lacking silanol groups," as outlined above, refers to a bioactive glass that is at least about 60% free, or about 75% free, or about 90-95% free of silanol groups.

Bioactive glass compositions can be maintained in a relative "dehydrated" state prior to use. The term "dry" as used herein can refer to compositions kept at ambient conditions, for example, at standard temperature, pressure, and humidity. It should be noted, however, that a "dry" compound can be provided in a substantially non-aqueous solvent (e.g., an alcohol). Thus, for example, slurries of bioactive glass powder in suitable non-aqueous solvent (e.g., an alcohol (e.g. ethanol)) are encompassed within the meaning of a "dry" bioactive glass composition. In some cases, the bioactive glass compositions may be stored in suitable packaging to keep the bioactive glass compositions dry (e.g. a sealed container).

Bioactive glass for use in the compositions and methods disclosed herein can be selected to have an average particle size that allows the bioactive glass particles to penetrate into the lumens of dentinal tubules. Dentinal tubules generally have diameters of approximately 0.8 µm to 1 µm before etching, and may have diameters of approximately 1 µm or greater after etching. Accordingly, suitable bioactive glass compositions for incorporation in the dental bonding slurry of the present disclosure include those having an average particle size of 1 µm or less, preferably 0.5 µm. Bioactive glass compositions can have a particle size distribution of at least 25%, at least 50%, at least 75%, at least 85%, or more (e.g., 99%) of the particles are of an average particle size of 1 µm or less.

Exemplary Bioactive Glasses are Described Below.
Bioglass 45S5 and Bioglass F (F Glass)

The invention can utilize two different bioglass compositions Bioglass F", or "F Glass", or Bioglass®. (45S5) in the slurry.

Bioglass formulation 45S5, or bioglass 45S5, is a bioactive glass that is composed of 49.5% $SiO_2$, 17.0% NaO, 26.9% CaO, and 6.6% $P2O_5$, all values are in weight %. Therefore, for example 6.6% of the total sample weight of Bioglass 45S5 would be $P_2O_5$.

Bioglass F formulation is composed of SiO2 (44%), Na2O (23%), CaO (10%), MgO (4.5%), P2O5 (6%), CaF2 (12.5%) all values are in weight %. Therefore, for example 12.5% of the total sample weight of Bioglass F would be CaF2.

In certain embodiments, bioglass 45S5 and Bioglass F is in a powder form, and can be provided as a dry powder. In these embodiments, the both bioglass powder is composed of nanoparticles with an average particle size of <1 µm or less and the preferred size is 0.5 µm or less. An average particle size of 1 µm or less allows the bioactive glass powder to penetrate into the lumens of dentinal tubules that have diameters of approximately 0.8 µm to 1 µm before etching and may have diameters of approximately 1 µm or more after etching. In addition, an average particle size of 1 µm or less can facilitate penetration of the bioactive glass into the partially etched intertubular dentin that has openings of less than 1 µm. Bioglass 45S5 powder may be prepared by methods known to those of skill in the art, including, but not limited to, planetary ball milling of bioglass 45S5 glass chips or utilization of planetary lapping equipment to grind the glass into fine particles.

F Glass

BioGlass F or F Glass is a bioactive glass that has the following approximate composition by weight percentage: $SiO_2$ (44%), $Na_2O$ (23%), CaO (10%), MgO (4.5%), $P_2O5$ (6%), and $CaF_2$ (12.5%). In certain embodiments, F glass is a powder, and can be provided as a dry powder. In these embodiments, the F glass powder may be composed of nanoparticles with an average particle size of less than 1 µm and preferable 0.5 µm of less. An average particle size of 1 µm or less allows the bioactive glass powder to penetrate the lumens of dentinal tubules, that have diameters of approximately 0.8 to 1 µm before etching and may have diameters of approximately 1 µm or more after etching or cleaned. In addition, an average particle size of 1 µm or less may allow the bioactive glass to penetrate the partially etched or cleaned intertubular dentin that has openings of less than 1 µm. F glass powder may be prepared by methods known to those of skill in the art, including, but not limited to, planetary ball milling of chips of F glass.

Bioglass 45S5 or Bioglass F powders may be prepared by methods known to those of skill in the art, including but not limited to planetary ball milling of Bioglass 45S5 glass chips or utilization of lapping technology.

Solvents

The solvent used to disperse the bioactive glass in the dental bonding slurry can be any suitable solvent available in the art. As described above, bioactive glasses elicit a series of chemical reactions when they are brought into contact with tissue or any aqueous environment that contains calcium and phosphate, leading to the formation of carbonated hydroxyapatite (HCA). Accordingly, the solvent can be described as a "non-aqueous solvent" referring to solvents that do not contain water as a predominant component, and include, for example, solvents that contain less than 10% water by volume, less than 5% water by volume, less than 1% water by volume, and may contain no detectable water. Such non-aqueous solvents, thus, have a water content that is sufficiently low to avoid reaction of the bioactive, glass so as to significantly generate silanol groups. Thus, in some cases, the solvent for the adhesive composition contains less than 5% to less than 1% water, and can substantially lack water. In certain embodiments, the solvent is an alcohol. In these embodiments, the alcohol solvent may be ethanol, isopropyl alcohol, or any other suitable alcohol. In other cases, suitable solvents may include acetone. In some cases, the non-aqueous solvent is other than acetone.

The amount of solvent used in the dental bonding slurry can vary according to the desired properties of the composition. For example, solvent can be added or removed (e.g., by vacuum or evaporation), so as to provide a final dental bonding slurry having a desired viscosity or consistency. For example, the composition can be flowable at ambient temperature, and may be of a consistency compatible with painting the composition onto the surface to be treated. Exemplary compositions can have the consistency of a fluid paste or gel. In general, the viscosity of the composition is compatible with its use so as to allow the composition to penetrate to a sufficient degree into the dentin matrix.

Bioactive Glass-Containing Dental Bonding Slurry or Use in Preparation and Dentin Repair Methods As noted above, dental bonding slurry or gel containing bioactive glass can include compounds to facilitate one or more steps of a dental bonding method according to the present disclosure. Thus, dental bonding slurry or gel can provide for activity as one or more of an etchant (as in, etching of dentin), a suitable non-aqueous solvent, bioglass, or combinations thereof (e.g., to provide for any combination (including all) steps of dental bonding methods). In these embodiments, the dental etchant may be an inorganic or organic acid, such as but not limited to phosphoric acid, maleic acid, or citric acid. However, the dentin can also be prepared by vigorous brushing with a suitable nylon brush to produce irregularities in the surface of dentin.

For example, in one embodiment, the dental bonding slurry can include a primer, a bioactive glass, chlorotoxin a powder form that can be added to the ethanol to form a slurry. A slurry of 20% or 40% (w/v) bioactive glass of the formulation 45S5 (Bioglass 45S5, SEM-COM, Toledo, Ohio) in ethanol mixture is preferred. The bioglass is initially prepared. The average particle size of the ground bioactive glass powder is less than 1 μm, and it was prepared by planetary ball milling of glass chips.

The ethanol mixture is prepared with ethanol with comprised of ethanol, 0.01% dove oil, 0.03% Cannabidiol (CBD) oil, 0.02% Boswellia and 0.001% chlorotoxin from a Blue Scorpion Venom Chlorotoxin. If aspirin (ASA) or other NSAID is to be used as the anti-inflammatory agent, the aspirin/NSAID would be loaded into the ethanol by weight equal to 0.05% aspirin. The scorpion venom chlorotoxin is added to the slurry 1-part venom 10,000 parts by weight of ethanol mixture, then the mixture is thoroughly mixed to ensure that all the ingredients are distributed within the mixture. The slurry is created by adding the Bioglass to the ethanol mixture such that it comprises of 20% of the slurry by weigh or 40% by volume. The slurry is then formed by mixing all the ingredients thoroughly to ensure that all the ingredients are distributed within the slurry.

The normal method of preparing the tooth is to prepared the tooth by using an etchant and exposing the dentin, then the process is to apply the slurry/gel so that it penetrates the dentinal tubules. The glass seal to the tubules to prevent microleakage and sensitivity. The next step is to rebuild the enamel, which is the outer surface of the tooth to protect the dentin and encase the glass. This process does not result in rapid bonding of the glass to the dentin and can result in inflammation and in some cases an infection. The instant invention use of clove oil, Cannabidiol (CBD) oil, Boswellia, aspirin or an NSAID and chlorotoxin is designed to overcome the problems currently experienced by patient. Secondly the instant invention uses an electromagnetic field to cure and increase the bond strength between the glass and the dentin by promoting the formation of carbonated hydroxyapatite (HCA).

If the application requires the use of a gel, then conventional gel formulations can be used such as a gel based on Carbomer 934, Sodium carboxymethylcellulose (SCMC) or a hydroxypropyl methylcellulose (HPMC).

Composition of Gel Formulations with Different Polymers (Carbomer 934, SCMC and HPMC $K_4M$)

TABLE 1

| Ingredients (g) | Formulation 1 | Formulation 2 | Formulation 3 |
|---|---|---|---|
| Carbomer 934 | 1 | = | = |
| Sodium CMC | — | 3 | — |
| HPMC $K_4M$ | — | — | 2 |
| Golnar extract | 12 | 12 | 12 |
| PEG 400 | 13 | 13 | 13 |
| Potassium Sorbate | 0.1 | 0.1 | 0.1 |
| Purified water to | 100 | 100 | 100 |

Preparation of SCMC Gel

Using the amounts on Table 1, potassium sorbate was dissolved in 50.degree. C. purified water. Then an exact amount of SCMC was slowly added to it while being mixed with magnetic stirrer in 1200 rpm for 30 minutes till it was completely homogenous. Then the ingredients clove oil, Cannabidiol (CBD) oil, Boswellia, aspirin or an NSAID and chlorotoxin is weighted and added to polyethylene glycol 400 (PEG 400). The extract was added slowly to the gel and mixed till uniform.

Preparation of HPMC Gel

Using the amounts on Table 1, potassium sorbate was dissolved in about one third of the formulation's water heated to 83.degree. C. and then a specific amount of HPMC was slowly added and mixed using magnetic stirrer in 1200 rpm. The remaining water was cooled and slowly added and mixed till a uniform gel was achieved. The gel remained in refrigerator overnight (hot/cold technique). Then an exact amount of concentrated pomegranate flower extract was separately added to PEG 400 and mixed and then gradually added to the gel.

Preparation of Carbomer 934 Gel

Using the amounts on Table 1, first potassium sorbate (as preservative) was dissolved in 40.degree. C. purified water and then a specific amount of carbomer 934 was mixed with it till homogenous using a magnetic stirrer with 1200 rpm for 30 minutes. A determined amount of concentrated punica extract was weighed and mixed well with PEG 400. This mixture was slowly added to the gel and mixed to achieve a uniform gel. While monitoring the pH, triethanolamine was added to the gel for it to reach a pH of about 6.

Resuming the disclosure of the invention with respect to a slurry. The slurry of the invention is applied to the exposed dentin and vacuum applied at 530 mm Hg for one minute; the sample surface was kept moist by re-applying the slurry every few seconds. After removal from the vacuum, any excess solid was gently rinsed away with deionized water.

Then an electromagnetic stimulator similar to that disclosed in U.S. Pat. No. 6,592,509 which the disclosure of is incorporated in its entirety by reference. The electromagnetic stimulator is placed over the patients head and proximal to the tooth or teeth being treated. The electromagnetic stimulator is connected to a direct current power supply. The electromagnetic stimulator consists of a coil. The voltage of the AC power supply is set to 12 volts AC and current flow through the coil is about four amps. The current is left on and the electromagnetic stimulator is allowed to bath the dental repair area for 1 to 10 minutes depending on the amount of curing that is desired. The electromagnetic stimulator increase the bond strength, bioactivity and promotes the formation of carbonated hydroxyapatite (HCA). Applying a device as described in U.S. Pat. No. 6,592,509 has been shown to improve healing and bone formation. U.S. Pat. No. 7,361,136 provides additional data that electromagnetic stimulation increases or restores the healing process. The objective of applying bioglass to the dentin is to increase the bond strength and promotes the formation of carbonated hydroxyapatite (HCA) which is affected by the electromagnetic stimulation which increases the healing process and the integration of the bioglass into the structure of the dentin. Otherwise the repair process of applying enamel over the exposed and treated dentin is depending on the healing to occur after the email is applied. By using the electromagnetic stimulator, we promote the integration of the bioglass with the dentin.

Other research has reinforced the use of bioglass materials. Some of the most promising biomaterials for application in bone tissue engineering are bio ceramics, such as hydroxyapatite (HA), calcium phosphates, bioactive glasses and related composite materials combining bioactive inorganic materials with biodegradable polymers.

As described in Bioactive Glass and Class-Ceramic Scaffolds for Bone Tissue Engineering Lutz-Christian Gerhardt 1 and Aldo R. Boccaccini—Bioactive inorganic materials are capable of reacting with physiological fluids forming tenacious bonds to bone through the formation of bone-like hydroxyapatite layers leading to effective biological interaction and fixation of bone tissue with the material surface. Moreover, in the case of silicate bioactive glasses, such as 45S5 Bioglass®, reactions on the material surface induce the release and exchange of critical concentrations of soluble Si, Ca, P and Na ions, which can lead to favorable intracellular and extracellular responses promoting rapid bone formation.

In addition, U.S. Patent application 20040086661 which the disclosure of is incorporated in its entirety by reference describes the process of sintering of bioactive glass with localized electromagnetic energy to limit disruption of organic material.

In these embodiments, the dental bonding slurry finds use in methods that include the sequential steps of: etching or cleaning with a suitable nylon bristle brush; and contacting the etched surface of dentin with the dental bonding slurry, such that the dental bonding slurry is applied to the etched surface of dentin. Thus, for example, the dental bonding slurry includes a bioactive glass and a non-aqueous solvent. In these embodiments, the dental bonding slurry may find use in methods that include contacting a tooth with the dental bonding slurry, such that the steps of etching and priming are achieved in a single application. In any of these embodiments, the method may further include contacting the etched and primed surface of dentin with an adhesive to facilitate the application of the dental bonding slurry as part of the restoration of teeth. It is imperative that the slurry is thoroughly mixed to ensure that all the ingredients are distributed within the slurry.

In other embodiments, the non-aqueous solvent such as ethanol includes; clove oil, Cannabidiol (CBD) oil, Boswellia and chlorotoxin from a Blue Scorpion Venom Chlorotoxin, aspirin (ASA) or other NSAID used as the anti-inflammatory agent and a primer, a bioactive glass of 0.1 µm or less and preferable less than 0.5 µm. In these embodiments, the dental bonding slurry may find use in methods that include contacting a tooth with an etchant to provide an etched dentin surface, and contacting the etched dentin with the dental bonding slurry, such that the steps of priming and dental bonding are achieved in a single application step.

In other embodiments, the dental bonding slurry includes a suspension (e.g., slurry) of a bioactive glass in a non-aqueous solvent. In these embodiments, the dental bonding slurry may find use in methods that include the steps of etching; contacting the etched surface of dentin with the dental bonding slurry; priming; and dental bonding.

In any of the above embodiments the solvent may be an alcohol, such as, but not limited to, ethanol.

Method of Snaking the Electromagnetic Stimulator

As depicted in FIG. 1 an electromagnetic stimulator device 2022 which is positionable about the region of dental work to be treated and AC source 2023 through which AC current is delivered to the stimulator device 2022. In addition, the system 2020 includes means, generally indicated 2024, for providing altering the current flow delivered to the device 2022 through cable 2021.

The stimulator device 2022 includes an electrically-conductive band 2026 which is sized to be positioned about the region of the dental work to be treated with the system 2020, the positive electrode 2028 from the power supply is attached to contact 2032 and the negative electrode 2029 is connected to contact 2034 wherein each contact 2032 or 2034 is connected to the coil 2021 and coil 2021 encircles a dental area being treated.

During use of the electromagnetic stimulator device 2022, AC current is delivered from source/generator 2023 through to the coil 2021 which, in turn, generates a corresponding electromagnetic field within the interior opening of the stimulator device 2022 so that by positioning the dental area being treated within the interior opening of the stimulator device 2022, the dental area being treated is exposed to the field established within the band stimulator device 2022. The electromagnetic stimulator increase the bond strength and promotes the formation of carbonated hydroxyapatite (HCA).

Methods of Leaking the Slurry

Methods for making a dental bonding slurry for dental bonding, in general, can involve combining a bioactive glass as described above with a suitable non-aqueous solvent such as ethanol, clove oil, Cannabidiol (CBD) oil, Boswellia and chlorotoxin from a Blue Scorpion Venom Chlorotoxin, aspirin (ASA) or other NSAID used as the anti-inflammatory agent and a primer, a bioactive glass of 1 µm or less preferably 0.5 µm or less (e.g., to generate a gel or slurry)

In certain cases, the method includes mixing a bioactive glass, as described above, such that it is combined with a non-aqueous solvent (e.g., acetone or an alcohol, such as, but not limited to, ethanol) clove oil, Cannabidiol (CBD) oil, Boswellia and chlorotoxin from a Blue Scorpion Venom Chlorotoxin, aspirin (ASA) or other NSAID used as the anti-inflammatory agent and a primer, prior to combining with the bioactive glass.

The types and amounts of bioactive glass as well as the types of solvent can be those as exemplified herein.

The methods for production of a dental bonding slurry contemplate production of intermediate compositions, that can later be combined to form the final dental bonding slurry. For example, the bioactive glass can be provided in a non-aqueous solvent in a first container. In another example, the bioactive glass can be provided as a powder in a first container and a non-aqueous solvent such as ethanol, clove oil, Cannabidiol (CBD) oil, Boswellia and chlorotoxin from a Blue Scorpion Venom Chlorotoxin, aspirin (ASA) or other NSAID used as the anti-inflammatory agent and a primer, provided in a second container. All or part of the contents of the two containers can then be combined prior to use, according to directions which can be optionally packaged with the containers.

Methods of Use

The dental bonding slurry/gels described herein may be used in dental restoration procedures to restore a tooth or teeth when there has been a significant loss of enamel and the dentin is exposed. Generally, the steps involved for dental bonding a tooth include etching the tooth, applying the priming and bioglass slurry to the tooth, so that it is infused into the dentinal tubules, applying proper electromagnetic field to the bioglass mixture so that the bond time is reduced and the bond between the bioglass and the treated dentin is increase. The electromagnetic stimulator increase the bond strength and promotes the formation of carbonated hydroxyapatite (HCA).

Effectively dental bonding of the tooth may require preparation of the tooth prior to dental bonding due to the hydrophilic nature of dental tissue, such as dentin. To facilitate the formation of a mechanical bond between the bioglass and dentin, the steps described herein of etching, brushing, priming, and dental bonding may be used.

Etching involves applying an acid to the surface of a tooth to superficially demineralize the apatite of dentin or prepared the dentin surface by vigorous brushing with a suitable nylon bristle brush to produce irregularities in the surface of dentin matrix.

Etching may also remove surface contaminants, also known as the "smear layer," on the surface of dentin, etching or brushing the dentin exposes a layer of collagen fibers. Removal of the smear layer also exposes the dentinal tubules. Etching increases the surface area available for dental bonding and facilitates penetration of the bioglass into the porosities in the dentin matrix revealed by the etching procedure. Penetration of the bioglass into the dentin matrix forms a hybrid layer that is composed of the dentin and the bioglass. This facilitates the formation of a mechanical bond between the dentin tubulars and the bioglass. Dental etchants may be an inorganic or organic acid such as, but not limited to, phosphoric acid, maleic acid, citric acid. Applying proper electromagnetic field to the bioglass mixture so that the bond time is reduced and the bond between the bioglass and the treated dentin is increase. The electromagnetic stimulator increase the bond strength and promotes the formation of carbonated hydroxyapatite (NCA).

The subsequent step of dental bonding the dental resin composite to the dentin with the dental bonding slurry may include contacting the, etched surface of dentin with the dental bonding slurry. Prior to contacting the etched and/or primed surface of dentin with the dental bonding slurry, the dental bonding slurry may be made as described herein. In some cases, the dental bonding slurry may be made in advance and stored until used. The dental bonding slurry may be stored in a sealed container, such that, during storage, the dental bonding slurry remains substantially free of water. However, to achieve a suitable bond in a timely manner an electromagnetic field needs to be applied to the bioglass mixture so that the bond time is reduced and the bond between the bioglass and the treated dentin is increase. The electromagnetic stimulator increase the bond strength, bioactivity and promotes the formation of carbonated hydroxyapatite (HCA) on the surface of the tooth.

Application of Bioactive Glass-Containing Suspension

In certain embodiments, the method includes the steps of etching which involves applying an acid to the surface of a tooth to superficially demineralize the apatite of dentin or prepared the dentin surface by vigorous brushing with a suitable nylon bristle brush to produce irregularities in the surface of dentin, contacting the surface of dentin with a slurry of a bioactive glass in a non-aqueous solvent containing clove oil, Cannabidiol (CBD) oil, Boswellia and chlorotoxin from a Blue Scorpion Venom Chlorotoxin, aspirin (ASA) or other NSAID used as the anti-inflammatory agent and a primer, and dental bonding. In these embodiments, the dentin is first brushed with a nylon bristle brush vigorously brushing the dentin exposes a layer of collagen fibers to remove the smear layer. Removal of the smear layer also exposes the dentinal tubules.

In these embodiments alternatively in place of brushing one could elect to use a dental etchant which may be an inorganic or organic acid, such as, but not limited to, phosphoric acid, maleic acid, or citric acid. Then, the cleaned dentin is contacted with a suspension of a bioactive glass (e.g., slurry) in a non-aqueous solvent. In some cases, the non-aqueous solvent may be an alcohol, such as, but not limited to, ethanol and the solvent has been formulated to contain a mixture of anti-inflammatory, antiinfection and pain relieve agents such as clove oil, Cannabidiol (CBD) oil, Boswellia and chlorotoxin from a Blue Scorpion Venom Chlorotoxin, aspirin (ASA) or other NSAID used as the anti-inflammatory agent may be contacted with a dental primer and cured with electromagnetic stimulator. The electromagnetic stimulator increase the bond strength and promotes the formation of carbonated hydroxyapatite (HCA).

Then, the primed surface of the dentin may be contacted with an adhesive. The adhesive may be cured as described herein. In some cases, the method also includes contacting the adhesive layer with a dental resin composite such that the dental resin composite is adhered to the dentin.

Kits

Also, of interest are kits for use in practicing certain embodiments of the invention. The components of the kits can be adapted for use in any of the various methods described herein.

Figure 2:
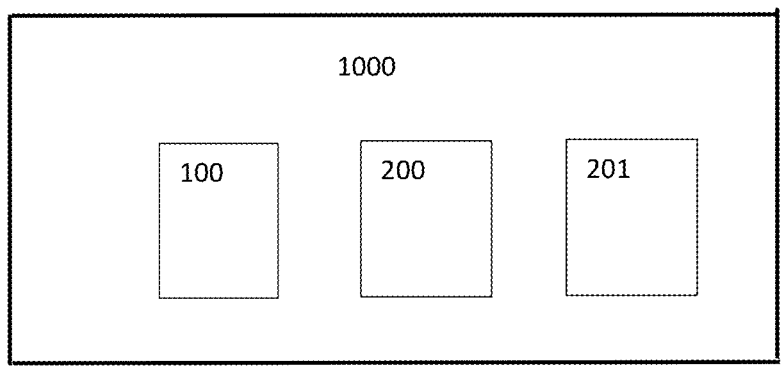
FIG. 2 shows a kit of the invention.

In certain embodiments, the kits can include a dental bonding slurry of the present disclosure, that may be provided for immediate use, or may be provided as separate components to be combined to form the dental bonding slurry. The dental bonding slurry can be provided in a container that can be adapted to facilitate application to an etched dentin surface. For example, the container can be in the form of a needleless syringe fitted with a plunger to provide for application of the contents of the container to an etched dentin surface, More specifically as shown in FIG. 2, A kit 1000 comprising: a dental bonding slurry 100 comprising a bioactive glass substantially lacking silanol groups; a non-aqueous solvent 200 comprising an alcohol and clove oil, Cannabidiol (CBD) oil, Boswellia and chlorotoxin from a Blue Scorpion Venom, aspirin (ASA) or other NSAID used as the anti-inflammatory agent; optionally, an etching composition 201 suitable for use with the dental bonding slurry.

For example, where the dental bonding slurry is provided as separate components (e.g., as described above in the context of methods of making the dental bonding slurry), the kit can include a first container containing a bioactive glass (e.g., powder) and a second container with a non-aqueous solvent including a mixture of clove oil, Cannabidiol (CBD) oil, Boswellia and chlorotoxin and other inflammation and pain agents such as Aspirin, or acetylsalicylic acid (ASA) or other NSAID pain relive medication a needed.

Optionally, the kit can include instructions for combining all or a portion of the first and second containers to provide a dental bonding slurry. Provided in a second container, all or part of the contents of the two containers can then be combined prior to use, according to directions that can be optionally provided with the kit. In one embodiment, where the dental bonding slurry is provided as separate components to be combined prior to use, the two components are maintained in separate containers that are not in fluid communication, but that are separated by a frangible or removable wall, that can be broken, or removed, to facilitate mixing of the two components prior to use.

The kits can optionally include additional components. For example, the kits can include one or both of an etchant, clove oil, Cannabidiol (CBD) oil, Boswellia and chlorotoxin from a Blue Scorpion Venom, aspirin (ASA) or other NSAID used as the anti-inflammatory agent and a primer compatible for use with the dental bonding slurry/gel. Such additional components can be provided in additional containers as may be desired.

Alternatively, the kits can optionally include additional. components. For example, the kits can include one or both of a bioglass, non-aqueous solvent such as ethanol, etchant, clove oil, Cannabidiol (CBD) oil, Boswellia, aspirin (ASA) used as the anti-inflammatory agent and a primer compatible for use with the dental bonding slurry.

The components included in the slurry/gel can be selected from bioglass, etchant, non-aqueous solvent such as ethanol, clove oil, Cannabidiol (CBD) oil, Boswellia, chlorotoxin from a Blue Scorpion Venom, aspirin (ASA), other NSAID and a primer compatible for use with the dental bonding slurry/gel. Such additional components can be provided in additional containers as may be desired.

In certain embodiments, the kit may include an etchant and a dental bonding slurry/gel of bioglass containing clove oil, Cannabidiol (CBD) oil, Boswellia and chlorotoxin from a Blue Scorpion Venom, aspirin (ASA) or other NSAID used as the anti-inflammatory agent in a non-aqueous solvent such as ethanol, where the etchant and the dental bonding slurry are provided in separate containers. In these embodiments the dental bonding slurry may include a bioactive glass and a solvent.

In other embodiments, the kit may include a dental bonding slurry provided in a single container. In some cases, the dental bonding slurry may include a bioactive glass and a solvent.

In certain embodiments, the, kits will further include instructions for practicing the subject methods or means for obtaining the same (e.g., a website URL directing the user to a webpage that provides the instructions), where these instructions may be printed on a substrate, where substrate may be one or more of a package insert, the packaging, reagent containers, and the like. In the subject kits, the one or more components are present in the same or different containers, as may be convenient or desirable.

EXAMPLES

The following examples are, put forth, so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Celsius, and pressure is at or near atmospheric.

Example 1

Figure 3:
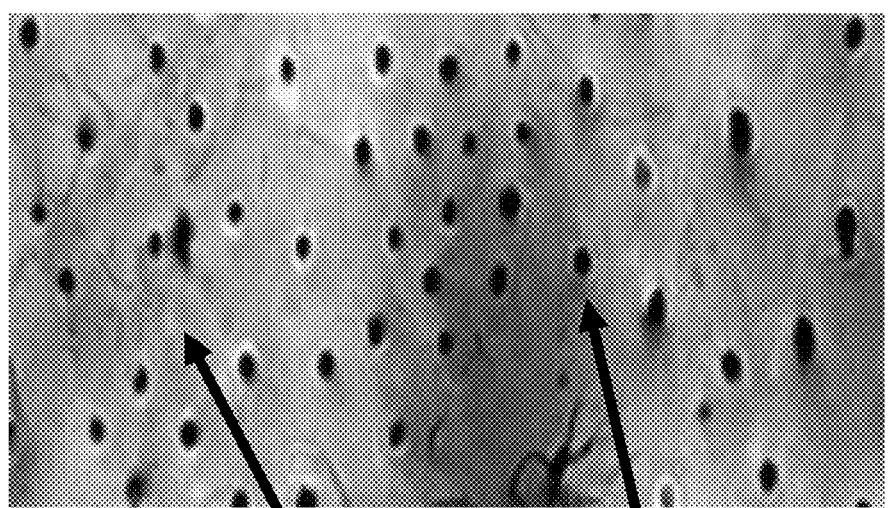
FIG. 3 shows scanning electron microscopy (SEM) micrographs untreated dentin.

Studies to, test the dental bonding of dentin in the presence of bioglass 45S5 were performed.
Preparation of Tooth Samples The occlusal enamel of six human third molars were removed using a belt sander with 240-grit silicon carbide paper, following which the roots were removed using a slow-speed saw (IsoMet®, Buehler Ltd., Lake Bluff, Ill.) with water coolant to produce tooth discs approximately 5 mm thick. The exposed dentin was polished with 320-grit silicon carbide paper. The discs were mounted on open-ended tubes with hot glue and attached to a vacuum trap. Scanning, electron micrographs were taken of the Sample 1 (shown in FIG. 3) presenting the dentin 10 and the dentinal tubule 20.

The occlusal dentin was cleaned with a nylon bristle brush by scrubbing the area for 15 seconds and rinsed for a further 15 seconds with deionized water. A slurry of 20% or 40% (w/v) bioactive glass of the formulation 45S5 (Bioglass 45S5, SEM-COM, Toledo, Ohio) which has the nominal approximate formula of 49.5% $SiO^2$, 17.0% NaO, 26.9% CaO, and 6.6% $P_2O_5$, all values are in weight %, in ethanol mixture is prepared with ethanol. The ethanol comprises of 0.01% by weight of clove oil, 0.03% by weight of Cannabidiol (CBD) oil, 0.02% by weight of Boswellia, aspirin (ASA) loaded into the ethanol by weight equal to 0.05% aspirin. Then the mixture is thoroughly mixed to ensure that all the ingredients are distributed within the mixture. The slurry is created by adding the Bioglass to the ethanol mixture such that it comprises of 20% of the slurry by weigh. The slurry is then formed by mixing all the ingredients thoroughly to ensure that all the ingredients are distributed within the slurry. Then the dentin is primed by scrubbing the exposed dentin with a suitable nylon bristle brush to produce irregularities in the surface of dentin The slurry was applied to the top of the sample. The average particle size of the ground bioactive glass powder was less than 1 μm, and it was prepared by planetary ball milling of glass chips. The glass slurry was prepared with ethanol which comprised of ethanol, 0.01% clove oil, 0.03% Cannabidiol (CBD) oil, 0.02% Boswellia. Vacuum was applied at 530 mm Hg for one minute after application to the dentin; the sample surface was kept moist by re-applying the slurry every few seconds. After removal from the vacuum, any excess solid was gently rinsed away with deionized water.

Then an electromagnetic stimulator is connected to an alternating current power supply. The electromagnetic stimulator consists of a coil, The voltage of the AC power supply is set to 12 volts AC and current flow through the coil is about four amps. The current is applied to the electromagnetic stimulator for up to 3 minutes to allow the electromagnetism to stimulate the dental repair area to cure the slurry/gel. The electromagnetic stimulator increase the bond strength, bioactivity and promotes the formation of carbonated hydroxyapatite (HCA).

Results

Figure 4:
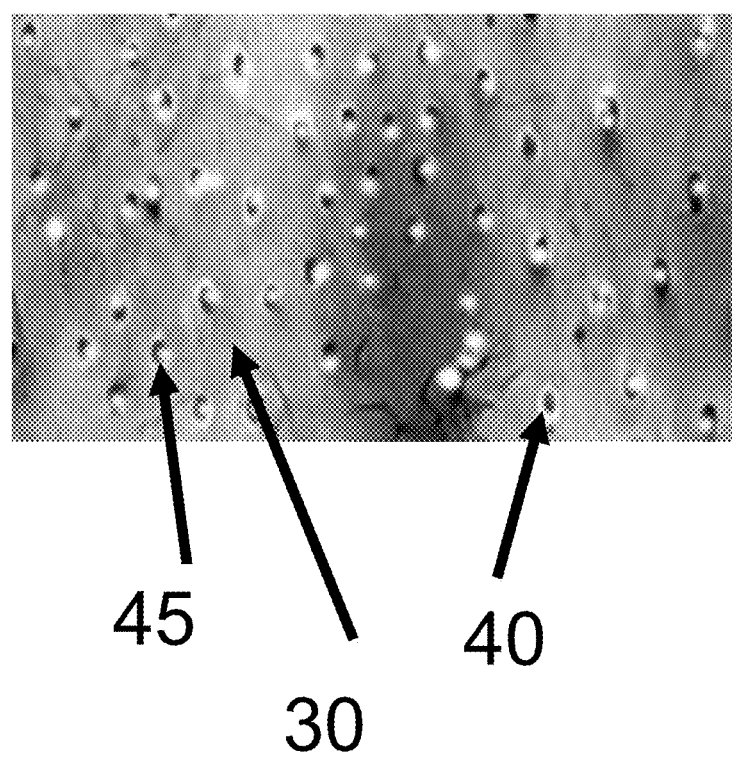
FIG. 4 shows SEM micrographs dentin treated with bioglass.

Following application of the bioglass,

Second scanning electron micrographs of Sample 1 taken are shown in FIG. 4 (dentin 30 and dentinal tubule 40) with a bioglass particle 45 in the tubule.

The above experiments showed that the bioactive glass are effectively incorporated into the resin-dentin dental bonding process. Once incorporated into the dentin, the microparticles of bioactive glass seal the dentin tubules to prevent sensitivity and microleakage, The electromagnetic stimulator stimulates the incorporation of the bioglass into the dentin and promotes the repair of the dentin. The electromagnetic stimulator increase the bond strength and promotes the formation of carbonated hydroxyapatite (HCA).

Example 2

Studies to Test the Dental Bonding of Dentin in the Presence of F Glass were Performed.

Preparation of Tooth Samples

Figure 5:
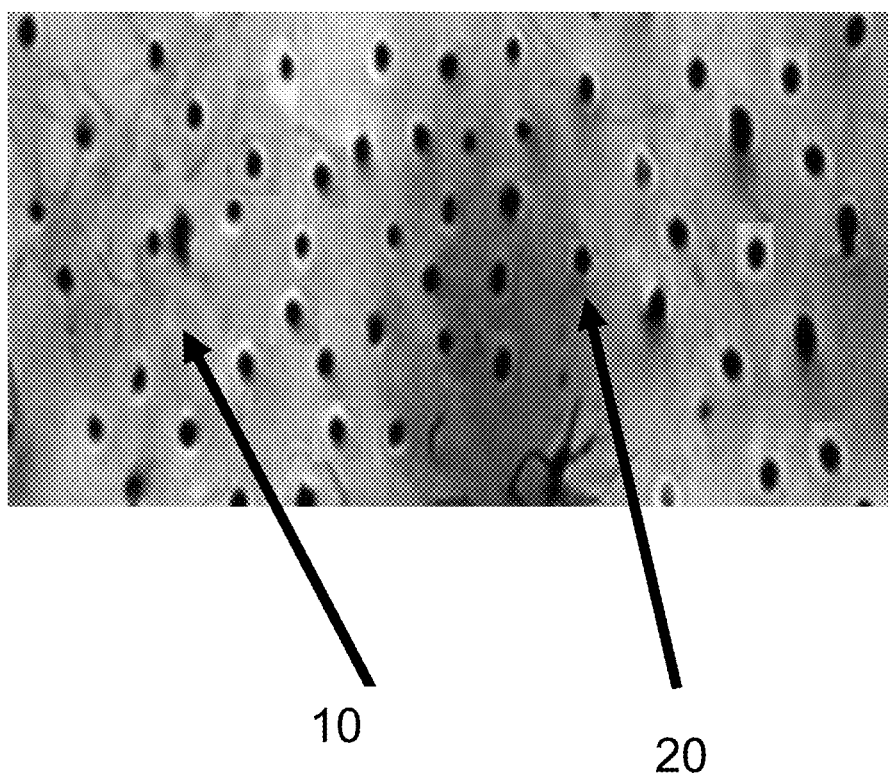
FIG. 5 shows scanning electron microscopy (SEM) micrographs untreated dentin.

The occlusal enamel of six human third molars were removed using a belt sander with 240-grit silicon carbide paper, following which the roots were removed using a slow-speed saw (IsoMet, Buehler Ltd., Lake Bluff, Ill.) with water coolant to produce tooth discs approximately 5 mm thick. The exposed dentin was polished with 320-grit silicon carbide paper. The discs were mounted on open-ended tubes with hot glue, and then attached to a vacuum trap. Scanning electron micrographs were taken of the Sample 2 (shown in FIG. 5) presenting the dentin 10 and the dentinal tubule 20.

The occlusal dentin of sample 2 was cleaned with a nylon bristle brush by scrubbing the area for 15 seconds and rinsed for a further 15 seconds with deionized water. A slurry of 40% weight of bioactive glass of the formulation Bioglass F or F Glass and has the following approximate composition by weight percentage: 44% of the total weight of bioactive glass comprising of $SiO_2$, 23% of the total weight of bioactive glass comprising of $Na_2O$, 10% of the total weight of bioactive glass comprising of CaO, 4.5% of the total weight of bioactive glass comprising of MgO, 6% of the total weight of bioactive glass comprising of $P_2O_5$, 12.5% of the total weight of bioactive glass comprising of $CaF_2$ in ethanol with 0.01% by weight of clove oil, 0.03% by weight of Cannabidiol (CBD) oil, 0.02% by weight of Boswellia and 0.001% by weight of chlorotoxin from a Blue Scorpion Venom Chlorotoxin and by weight of 0.05% aspirin. The slurry is created by adding the Bioglass to the ethanol mixture such that it comprises of 40% of the slurry by volume. The glass and ethanol mixture is mixed thoroughly to create a slurry. The slurry was applied to the top of the sample by brushing. The average particle size of the ground bioactive glass powder was approximately 0.5 µm, and it was prepared by high energy ball milling of glass chips. The glass slurry was prepared with ethanol. Vacuum was applied at 530 mm Hg for one minute after the slurry was applied to the dentin by brushing; the sample surface was kept moist by re-applying the slurry every few seconds. After removal from the vacuum, any excess solid was gently rinsed away with deionized water.

Then an electromagnetic stimulator is connected to an alternating current power supply. The electromagnetic stimulator consists of a coil. The voltage of the AC power supply is set to 12 volts AC and current flow through the coil is about four amps. The current is applied to the electromagnetic stimulator for up to 3 minutes to allow the electromagnetism to stimulate the dental repair area to cure the slurry/gel. The electromagnetic stimulator increase the bond strength, bioactivity and promotes the formation of carbonated hydroxyapatite (HCA).

Results

Figure 6:
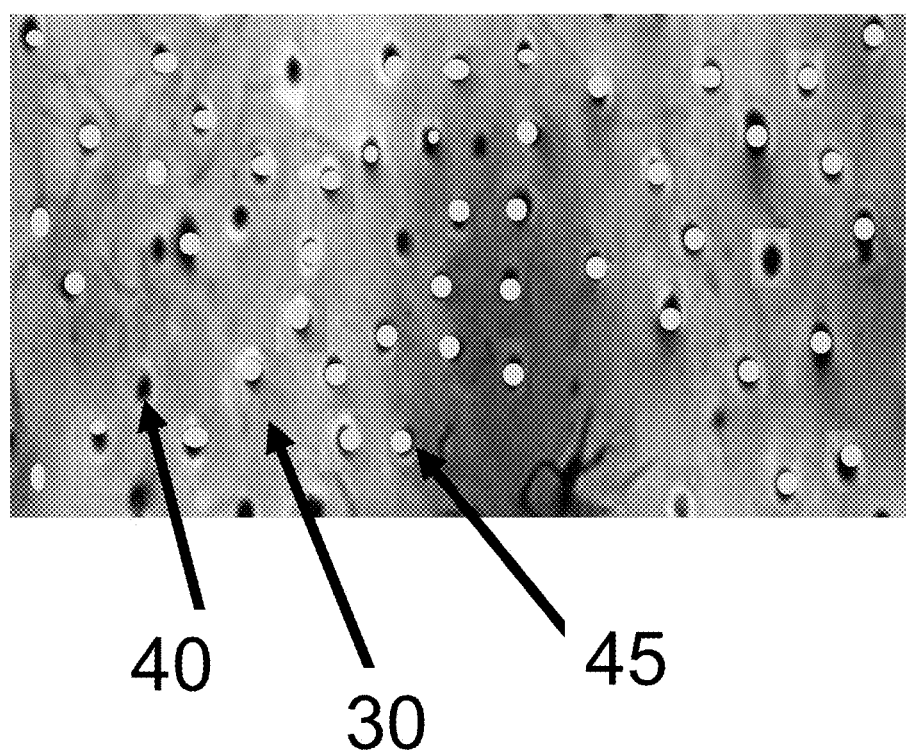
FIG. 6 shows SEM micrographs dentin treated with bioglass.

Following application of the bioglass,

Second scanning electron micrographs of Sample 2 taken are shown in FIG. 6 (dentin 30 and dentinal tubule 40) with a bioglass particle 45 in the tubule.

The above experiments showed that the bioactive glass are effectively incorporated into the resin-dentin dental bonding process. Once incorporated into the dentin, the microparticles of bioactive glass seal the dentin tubules. The electromagnetic stimulator stimulates the incorporation of the bioglass into the dentin and promotes the repair of the dentin and increases the bond strength and promotes the formation of carbonated hydroxyapatite (HCA).

Testing of the Slurry for Reduced Pain and Inflammation.

The first slurry is formulated such that 20% by weight of bioactive glass of the formulation is 45S5 (Bioglass 45S5, SEM-COM, Toledo, Ohio) having a nominal approximate formulation of which has the nominal approximate formula of 49.5% $SiO_2$, 17.0% NaO, 26.9% CaO, and 6.6% $P_2O_5$, all values are in weight %, and the second part being an ethanol mixture that is prepared of ethanol and the following additional ingredients, 0.01% by weight of clove oil, 0.03% by weight of Cannabidiol (CBD) oil, 0.02% by weight of Boswellia and 0.001% by weight of chlorotoxin from a Blue Scorpion Venom Chlorotoxin, aspirin (ASA) loaded into the ethanol by weight equal to 0.05% aspirin. Then the mixture is thoroughly mixed to ensure that all the ingredients are distributed within the mixture. The slurry is created by adding the Bioglass to the ethanol mixture such that it comprises of 20% of the slurry by weigh. The slurry is then formed by mixing all the ingredients thoroughly to ensure that all the ingredients are distributed within the slurry.

The second slurry was formulated to create a slurry of 20% weigh of bioactive glass of the formulation 45S5 (Bioglass 45S5, SEM-COM, Toledo, Ohio) in ethanol. The slurry is created by adding the Bioglass to the ethanol such that it comprises of 20% of the slurry by weigh. The slurry is then formed by mixing all the ingredients thoroughly to ensure that all the ingredients are distributed within the slurry.

Then a patient had two teeth with exposed dentin prepared by cleaning with a nylon bristle brush by scrubbing the area for 15 seconds and rinsed for a further 15 seconds with deionized water. The patient was asked to rate the pain level of both cleanings and rated the level of pain on a 1 to 10 scale for both teeth and the patient rated the pain as a 6.

The then first slurry was applied to one of the patients teeth. And vacuum was applied at 530 mm Hg for one minute; the sample surface was kept moist by re-applying the slurry every few seconds. After removal from the vacuum, any excess solid was gently rinsed away with deionized water.

Then an electromagnetic stimulator is connected to an alternating current power supply. The electromagnetic stimulator consists of a coil. The voltage of the AC power supply is set to 12 volts AC and current flow through the coil is about four amps. The current is left on and the electromagnetic stimulator is allowed to bath the dental repair area for 3 minutes to cure the slurry. The electromagnetic stimulator increase the bond strength and promotes the formation of carbonated hydroxyapatite (HCA).

The patient was asked to rate the pain level of both cleanings and rated the level of pain on a 1 to 10 scale for both teeth and the patient rated the pain as a 2.

The then second slurry was applied to the second tooth of the patients. And vacuum was applied at 530 mm Hg for one minute; the sample surface was kept moist by re-applying the slurry every few seconds. After removal from the vacuum, any excess solid was gently rinsed away with deionized water.

Then an electromagnetic stimulator is connected to an alternating current power supply. The electromagnetic stimulator consists of a coil. The voltage of the AC power supply is set to 12 volts AC and current flow through the coil is about four amps. The current is left on and the electromagnetic stimulator is allowed to bath the dental repair area for 3 minutes to cure the slurry. The electromagnetic stimulator increase the bond strength and promotes the formation of carbonated hydroxyapatite (HCA).

The patient was asked to rate the pain level of both cleanings and rated the level of pain on a 1 to 10 scale for both teeth and the patient rated the pain as a 7.

The results of the pain test demonstrated the advantage of the addition of 0.01% by weight of clove oil, 0.03% by weight of Cannabidiol (CBD) oil, 0.02% by weight of Boswellia and 0.001% by weight of chlorotoxin from a Blue Scorpion Venom Chlorotoxin, aspirin (ASA) loaded into the ethanol by weight equal to 0.05% aspirin to the ethanol.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

In addition, the present invention has been described with reference to embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

Although very narrow claims are presented herein, it should be recognized that the scope of this invention is much broader than presented by the claim. It is intended that broader claims will be submitted in an application that claims the benefit of priority from this application.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A kit for repairing dentin of a tooth comprising:
   a dental bonding slurry wherein said dental bonding slurry comprising a bioactive glass substantially lacking silanol groups;
   a non-aqueous solvent comprising alcohol, natural products and an anti-inflammatory agent;
   an etching composition; and
   an electromagnetic stimulator capable of using an alternating current (AC) voltage.

2. The kit for repairing the dentin of a tooth of claim 1, wherein said anti-inflammatory agent is selected from the group consisting of acetylsalicylic acid (ASA), Neem, Nimba, *Punica granatum*, Mentha spp. clove oil, Cannabidiol (CBD) oil, Boswellia and chlorotoxin.

3. The kit for repairing the dentin of a tooth of claim 2, wherein said chlorotoxin is venom selected from the group of scorpions consisting of emperor scorpion (*Pandinus imperator*), *Heterometrus swammerdami* scorpion, African *Androctonus australis, Hadrurus hirsutus*, Albino Scorpions, Black Scorpions or Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions and Whip Scorpions.

4. The kit for repairing the dentin of a tooth of claim 1, wherein the total weight percent of said bioactive glass substantially lacking silanol groups is 49.5% $SiO_2$, 17.0% NaO, 26.9% CaO, and 6.6% $P_2O_5$, 49.5% $SiO_2$, 17.0% NaO, 26.9% CaO, and 6.6% $P_2O_5$.

5. The kit for repairing the dentin of a tooth of claim 1, wherein the total weight percent of said bioactive glass substantially lacking silanol groups is $SiO_2$ (44%), $Na_2O$ (23%), CaO (10%), MgO (4.5%), $P_2O_5$(6%), and $CaF_2$ (12.5%).

6. The kit for repairing the dentin of a tooth of claim 1, wherein said alcohol is ethanol.

7. The kit for repairing the dentin of a tooth of claim 1, wherein said natural products is selected from the group consisting of Neem (*Azadirachta indica*), azadirachtin, nimbolinin, nimbin, nimbidin, nimbidol, salannin, and quercetin.

8. The kit for repairing the dentin of a tooth of claim 1, wherein said electromagnetic stimulator said alternating current voltage is 12 volts.

\* \* \* \* \*